United States Patent
Tournilhac et al.

(10) Patent No.: US 8,530,671 B2
(45) Date of Patent: Sep. 10, 2013

(54) METHOD FOR PREPARING A MATERIAL FORMED FROM ARBORESCENT-BRANCHED MOLECULES COMPRISING ASSOCIATIVE GROUPS

(75) Inventors: François-Genes Tournilhac, Paris (FR); Manuel Hidalgo, Brignais (FR); Ludwik Leibler, Paris (FR)

(73) Assignees: Arkema France, Colombes (FR); Centre National de la Recherche Scientifique CNRS, Paris Cedex (FR)

( * ) Notice: Subject to any disclaimer, the term of this patent is extended or adjusted under 35 U.S.C. 154(b) by 124 days.

(21) Appl. No.: 12/810,179

(22) PCT Filed: Dec. 19, 2008

(86) PCT No.: PCT/FR2008/052379
§ 371 (c)(1),
(2), (4) Date: Jun. 23, 2010

(87) PCT Pub. No.: WO2009/081065
PCT Pub. Date: Jul. 2, 2009

(65) Prior Publication Data
US 2010/0305334 A1   Dec. 2, 2010

(30) Foreign Application Priority Data
Dec. 24, 2007  (FR) ..................................... 07 60341

(51) Int. Cl.
*C07D 233/70*  (2006.01)
(52) U.S. Cl.
USPC ..................................................... 548/324.5
(58) Field of Classification Search
None
See application file for complete search history.

(56) References Cited

U.S. PATENT DOCUMENTS

| | | | | |
|---|---|---|---|---|
| 2,727,016 | A | * | 12/1955 | Hankins ......................... 526/263 |
| 5,700,576 | A | * | 12/1997 | Brehm et al. .................. 428/412 |
| 7,250,487 | B2 | * | 7/2007 | Tournilhac et al. ........... 528/422 |
| 2010/0135940 | A1 | * | 6/2010 | Grimaldi et al. ................ 424/62 |

FOREIGN PATENT DOCUMENTS

| | | |
|---|---|---|
| WO | 03059964 A2 | 7/2003 |
| WO | 2006087475 A1 | 8/2006 |
| WO | 2006/115547 A2 | 11/2006 |

OTHER PUBLICATIONS

Hankins et al., caplus an 1956:571157.*
World Intellectual Property Organization. "International Search Report" PCT/FR2008/052379. Applicant: Arkema France and Centre National de la Recherche. Mailed Aug. 4, 2009.
Brunsveld L et al: "Supramolecular polymers." (Chemical Reviews), Dec. 1, 2001; pp. 4071-4097, vol. 101.

* cited by examiner

*Primary Examiner* — Sun Jae Loewe
(74) *Attorney, Agent, or Firm* — Millen, White, Zelano & Branigan, P.C.

(57) ABSTRACT

The present invention relates to a method of preparing a material formed from arborescent-branched molecules comprising associative groups that includes the following successive steps: (a) the reaction of at least one at least trifunctional compound (A) bearing first and second functional groups with at least one bifunctional compound (B), the functional groups of which are capable of reacting with the first functional groups of the compound (A); and (b) the reaction of the compound(s) obtained in step (a) with at least one compound (C) bearing, on the one hand, at least one reactive group capable of reacting with the second functional groups of (A) and, on the other hand, at least one given associative group.

14 Claims, No Drawings

METHOD FOR PREPARING A MATERIAL FORMED FROM ARBORESCENT-BRANCHED MOLECULES COMPRISING ASSOCIATIVE GROUPS

The present invention relates to a novel method for preparing supramolecular materials.

So-called supramolecular materials are materials constituted by compounds linked together by non-covalent bonds, such as hydrogen bonds, ionic and/or hydrophobic bonds. One advantage of these materials is that these physical bonds are reversible, in particular under the influence of temperature or by the action of a selective solvent. It is thus possible to envisage using them in fields of application such as coatings (paints, cosmetics etc.), adhesives, hot-melt glues and powder paints.

Some of them moreover possess elastomeric properties. Unlike standard elastomers, these materials have the advantage of being able to become fluid above a certain temperature, which facilitates their utilization, in particular good mould filling, as well as their recycling. Although they are not constituted by cross-linked polymers but by small molecules, these materials are, like the elastomers, capable of exhibiting dimensional stability over very long periods and of recovering their initial shape after significant deformation. They can be used for manufacturing seals, thermal or acoustic insulation, tyres, cables, cladding, soles of footwear, packaging, patches (cosmetic or dermo-pharmaceutical), wound dressings, flexible hose clips, vacuum tubes, pipes and hoses for conveying fluids.

Methods for preparing supramolecular materials have already been described by the Applicant.

Thus, document WO 03/059964 describes a supramolecular material obtained by reacting urea with polyalkylene imines, polyamines or polyamides having in common that they contain free primary or secondary amine functions. The prepolymer obtained can in particular bear imidazolidone functions and free primary or secondary amine functions which can then react with an alkyl halide. The polyamides can themselves be obtained by condensation of polyamines with dimers and trimers of fatty acids.

Moreover, document WO 2006/016041 discloses a supramolecular material obtained by grafting compounds bearing an imidazolidone group, such as N-aminoethyl-2-imidazolidone (UDETA) onto a polymer such as a PMMA bearing anhydride functions.

A supramolecular elastomeric material is moreover disclosed in document WO 2006/087475. It comprises molecules containing at least three associative functional groups, such as imidazolidone groups, which are capable of forming several physical bonds and which can be obtained by reacting urea with the product of the reaction of a polyamine with triacids.

The drawback of the preparation methods of the prior art is that they require the use of urea which leads to a release of ammonia. Moreover, in order to obtain an elastomeric material as described in Application WO 2006/087475, it is necessary to strictly control the operating conditions such as the purity of the reagents, their order of introduction, the duration and the temperature of the reactions, as well as the homogeneity of the mixture. In particular, the oligoamidoamine derived from the fatty acid obtained by polycondensation of a polyamine such as diethylene triamine, DETA, or triethylene tetra-amine, TETA, and a fatty acid must meet very specific criteria in terms of purity and degree of polycondensation in order to produce an elastomer.

The Applicant has now developed a novel method for the synthesis of supramolecular materials which is easy to implement and does not lead to a release of ammonia, unlike the methods using urea as a reagent. This method also makes it possible to obtain materials containing molecules having a particular branched structure which can endow them with very varied properties depending on the proportions of the reagents used for their synthesis. Thus, depending on the number of reactive functions present in the initial compounds and the number of reactive functions remaining on completion of the first stage of synthesis, numbers that can easily be adjusted by the choice of starting materials and by use of an appropriate stoichiometric ratio, it is possible to obtain, by choice and in a controlled manner, a semi-crystalline or amorphous solid, a viscoelastic liquid or also an elastomeric material which is optionally thermoplastic. More precisely, when the average functionality of the monomers is not very high, essentially linear molecules are produced, having viscoelastic behaviour and which can optionally have a semi-crystalline or amorphous solid phase, whereas networks optionally containing an insoluble fraction and exhibiting elastomeric properties form when this functionality is high. It is also possible to obtain materials offering a compromise of properties such as capacity for self-repair/creep resistance or fluidity/tear strength.

Therefore, in particular, it is possible to obtain a material having the properties of a thermoplastic elastomer, i.e. a material capable, at ambient temperature, of being subjected to uniaxial deformation, advantageously of at least 20% for 15 minutes, then of recovering its initial dimension once the stress is removed, with a permanent deformation less than 5% of its initial dimension, and which can be formed or re-formed at high temperature. The novel method according to the invention can moreover make it possible to obtain self-healing materials, i.e. capable, once cut, torn or scratched, of repairing themselves by simply bringing the fractured surfaces back into contact without requiring heating or the application of significant pressure or carrying out any chemical reaction, the material thus repaired retaining elastomeric properties.

The method according to the invention consists of reacting, in a first step, a first compound containing a high proportion of molecules which are at least trifunctional with a second at least bifunctional compound, in non-stoichiometric proportions allowing free functions to remain on the first compound, in order to obtain a material that is reacted, in a second step, with a compound bearing one or more associative groups.

A subject of the present invention is therefore a method for preparing a material formed from arborescent-branched molecules comprising associative groups comprising the following successive steps:

(a) the reaction of at least one compound that is at least trifunctional (A), bearing first and second functions with at least one compound that is at least bifunctional (B), the functions of which are capable of reacting with the first functions of compound (A);

(b) the reaction of the compound or compounds obtained in step (a) with at least one compound (C) bearing, on the one hand, at least one reactive group capable of reacting with the second functions of (A) and, on the other hand, at least one associative group, said compound (C) corresponding to formula (C1), (C2) or (C3):

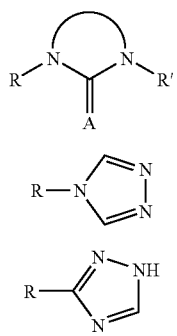

where

R denotes a unit containing at least one primary or secondary amine or alcohol group, R' denotes a hydrogen atom, A denotes an oxygen or sulphur atom or an —NH group, preferably an oxygen atom.

This method makes it possible to obtain a material comprising arborescent-branched molecules each constituted by fragments that are at least bifunctional and by fragments that are at least trifunctional joined to each other by first bridges, preferably ester or thioester, alone or in combination with second bridges, advantageously amide or urea, said first and second bridges being formed from two functions borne by different fragments, said molecules also comprising, on the fragments situated at the ends of the branches, associative end groups capable of linking together by hydrogen bonds and covalently linked to the functions not involved in said bridges. This material has reversible hydrogen bonds precisely between said associative groups.

By "arborescent-branched" is meant according to the invention a branched molecule the backbone of which comprises at least two branchings. This definition does not exclude the possibility of various branchings of the same molecule joining together to form loops.

By "associative groups", is meant groups capable of forming associations with each other by hydrogen bonds, advantageously by 1 to 6 hydrogen bonds. Examples of associative groups which can be used according to the invention are the imidazolidinyl, triazolyl, triazinyl, bis-ureyl and ureido-pyrimidyl groups. The average number of associative end groups per molecule of the material is preferably at least 3. It is advantageously at most 6. The latter are linked covalently to the molecule. By "covalently", is meant that the associative groups are connected to the end functions of the molecule either via a direct bond or, preferably, via a chain, in particular alkylene.

By "reactive groups" or "functions", is meant chemical functions capable of reacting with other chemical functions to form covalent bonds, leading in particular to the formation of ester, thioester, amide or urea bridges, and in particular ester and amide bridges. A compound that is "at least bifunctional" denotes a compound bearing at least two, and preferably only two, reactive functions that are identical or different. A compound that is "at least trifunctional" denotes a compound bearing at least three, and preferably only three, reactive functions that are identical or different.

By "fragment", is meant within the meaning of the invention a unit of a molecule located between two or three bridges as defined above. A "bifunctional" fragment is capable of being obtained from a bifunctional compound and a "trifunctional" fragment is capable of being obtained from a trifunctional compound. The arborescent-branched molecules according to the invention contain fragments that are at least bifunctional, advantageously bifunctional, and fragments that are at least trifunctional, advantageously trifunctional.

Compound (A) utilized in the first step of the method according to the invention can in particular bear at least three functions, identical or different, chosen from the acid, ester or acyl chloride functions. It advantageously comprises from 5 to 100, preferably from 12 to 100 and more preferentially from 24 to 90 carbon atoms.

Compound (A) can, in the first step of the method according to the invention, be mixed with mono- and bifunctional compounds, such as mono- and diacids, in particular monomers and dimers of fatty acids.

It is preferable to use trimers (oligomers of 3 identical or different monomers) and mixtures of dimers and trimers of fatty acids of vegetable origin. These compounds result from the oligomerization of unsaturated fatty acids such as: undecylenic, myristoleic, palmitoleic, oleic, linoleic, linolenic, ricinoleic, eicosenoic, docosenoic acid, that are usually found in pine oils (tall oil fatty acids), colza oil, maize oil, sunflower oil, soya oil, grape seed oil, linseed oil, jojoba oil, as well as the eicosapentaenoic and docosahexaenoic acids that are on found in fish oils.

As an example of trimers of fatty acids, there may be mentioned the compound of the following formula which illustrates a cyclic trimer originating from fatty acids with 18 carbon atoms, knowing that the commercially available compounds are mixtures of steric isomers and positional isomers of these structures, optionally partially or fully hydrogenated.

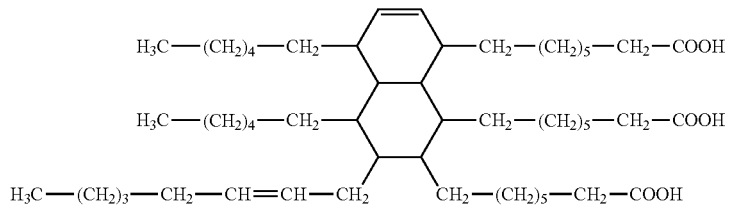

Trimer of C18 acid

It is thus possible to use a mixture of oligomers of fatty acids containing dimers, trimers and monomers of linear or cyclic $C_{18}$ fatty acids, said mixture being mainly of dimers and trimers and containing a small percentage (usually less than 5%) of monomers. Preferably, said mixture comprises:

0.1 to 40% by weight, preferably 0.1 to 5% by weight monomers of identical or different fatty acids, 0.1 to 99% by weight, preferably 18 to 85% by weight dimers of identical or different fatty acids and 0.1 to 90% by weight, preferably 5 to 85% by weight, trimers of identical or different fatty acids.

There may be mentioned, as examples of dimer/trimer mixtures of fatty acids (% by weight):

Pripol® 1017 from Uniqema, mixture of 75-80% dimers and 18-22% trimers with of the order of 1-3% monomeric fatty acids, Pripol® 1048 from Uniqema, mixture of 50/50% dimers/trimers, Pripol® 1013 from Uniqema, mixture of 95-98% dimers and 2-4% trimers with a maximum of 0.2% monomeric fatty acids, Pripol® 1006 from Uniqema, mixture of 92-98% dimers and a maximum of 4% trimers with a maximum of 0.4% monomeric fatty acids, Pripol® 1040 from Unigema, mixture of dimers and trimers of fatty acid with at least 75% trimers and less than 1% monomeric fatty acids, Unidyme® 60 from Arizona Chemicals, mixture of 33% dimers and 67% trimers with less than 1% monomeric fatty acids, Unidyme® 40 from Arizona Chemicals, mixture of 65% dimers and 35% trimers with less than 1% monomeric fatty acids, Unidyme® 14 from Arizona Chemicals, mixture of 94% dimers and less than 5% trimers and other higher oligomers with of the order of 1% monomeric fatty acids, Empol® 1008 from Cognis, mixture of 92% dimers and 3% higher oligomers, essentially trimers, with of the order of 5% monomeric fatty acids, Empol® 1018 from Cognis, mixture of 81% dimers and 14% higher oligomers, being essentially trimers, with of the order of 5% monomeric fatty acids, Radiacid® 0980 from Oleon, mixture of dimers and trimers with at least 70% trimers.

The products Pripol®, Unidyme®, Empol®, and Radiacid® contain monomers of $C_{18}$ fatty acids and oligomers of fatty acids corresponding to multiples of $C_{18}$.

According to a variant of the invention, instead of triacids, it is possible to use, as compound (A), a compound containing at least three ester or acyl chloride functions.

As an example of ester, there may be mentioned a methyl, ethyl or isopropyl ester (preferably methyl) of a trimer of fatty acid or of a mixture of oligomers of fatty acids as defined above.

In another variant, compound (A) can be a compound that is at least trifunctional containing at least two different functions, advantageously chosen from the acid, ester and acyl chloride functions.

For its part, compound (B) contains at least two functions, identical or different, capable of reacting with compound (A), chosen in particular from the epoxy, alcohol and amine functions. It can also include other functions that are not capable of reacting with compound (A).

Compound (B) is preferably a diepoxide. It can therefore be chosen from: bisphenol A diglycidyl ethers, bisphenol F diglycidyl ether, tetrabromo bisphenol A diglycidyl ether, or hydroquinone diglycidyl ethers, ethylene glycol diglycidyl ether, propylene glycol diglycidyl ether, butylene glycol diglycidyl ether, neopentyl glycol diglycidyl ether, 1,4-butanediol diglycidyl ether, 1,6-hexanediol diglycidyl ether, cyclohexanedimethanol diglycidyl ether, polyethylene glycol diglycidyl ether, polypropylene glycol diglycidyl ether, polytetramethylene glycol diglycidyl ether, resorcinol diglycidyl ether, neopentylglycol diglycidyl ether, bisphenol A polyethylene glycol diglycidyl ether, bisphenol A polypropyleneglycol diglycidyl ether, terephthalic acid diglycidyl ester, and mixtures thereof.

In a variant, compound (B) can be a polyepoxide containing at least three epoxide functions, chosen for example from: castor oil triglycidyl ether, 1,1,1-tris(hydroxymethyl) propane triglycidyl ether, trisphenol triglycidyl ether, glycerol triglycidyl ether, glycerol propoxylate triglycidyl ether, glycerol ethoxylate triglycidyl ether, trimethylol propane triglycidyl ether, sorbitol polyglycidyl ether, polyglycerol polyglycidyl ether, pentaerythritolpolyglycidyl ether, poly (glycidyl acrylate), polyglycidyl methacrylate, epoxidized polyunsaturated fatty acids, epoxidized vegetable oils, epoxidized fish oils and epoxidized limonene.

In yet another variant, compound (B) can be a diol. In this case, compound (B) can be chosen from: ethylene glycol, propylene glycol, tetramethylene glycol, hexamethylene glycol, octanediol, nonanediol, decanediol, diethylene glycol, dipropylene glycol, triethylene glycol, tetraethylene glycol, polyethylene glycol, polypropylene glycol, polytetramethylene glycol, polyesters with hydroxy ends, polybutadienes with hydroxy ends, polydimethylsiloxanes with hydroxy ends, polyisobutylenes with hydroxy ends, polybutadiene-co-acrylonitrile copolymers with hydroxy ends, diol dimers originating from fatty acids and mixtures thereof.

According to another possibility, compound (B) can be a polyol containing at least three alcohol functions. Examples of such compounds are in particular: sugars such as sorbitol, pentaerythritol, trimethylolpropane, as well as glycerol and its ethoxylated and propoxylated derivatives, castor oil and diol diners originating from fatty acids such as Pripol 2033 from Uniqema.

In the case where the functions of compound (B) are capable of reacting both with the first and second functions of compound (A), it is preferable that, in the first step of the method according to the invention, the ratio of the number of the reactive functions of compound (B) to the sum of the functions of compound (A) ranges from 0.1 to 0.8 and preferably from 0.3 to 0.8.

The compound obtained on completion of the first step of the method according to the invention is reacted, in the second step, with a compound (C) bearing at least one reactive group and at least one associative group, so that the reactive groups of (C) react with the second functions, i.e. the remaining reactive functions of compound (A).

Compound (C) bears at least one reactive group which can in particular be chosen from the primary or secondary amine or alcohol groups. In a variant, compound (C) can bear at least two such identical or different groups. It also bears an associative group chosen from the nitrogenous, preferably diazotized heterocycles. Compound (C) corresponds more precisely to any one of formulae (C1) to (C3):

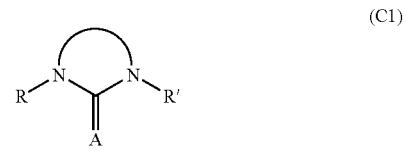

(C1)

(C2)

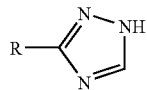
(C3)

where
R denotes a unit containing at least one primary or secondary amine or alcohol group,
R' denotes a hydrogen atom,
A denotes an oxygen or sulphur atom or an —NH group, preferably an oxygen atom.

Preferred examples of compounds (C) are 2-aminoethylimidazolidone (UDETA), 1-(2-[(2-aminoethyl)amino]ethyl)imidazolidone (UTETA), 1-(2-{2-[(2-aminoethylamino]ethyl}amino)ethyl]imidazolidone (UTEPA), 3-amino-1,2,4-triazole (3-ATA) and 4-amino-1,2,4-triazole (4-ATA).

It is understood that the material according to the invention comprises binding bridges, preferably ester, formed in the first step of its synthesis method, by reaction of the functions (advantageously epoxide) of compound (B) with reactive functions, so-called "first functions" (advantageously acid functions), of compound (A) and of the binding bridges (advantageously amide), formed in the second step of this method, by reaction of the remaining reactive functions (preferably acid), so-called "second functions", of compound (A) with reactive groups (advantageously amine) of compound (C). This material also contains hydrogen bonds between the associative groups borne by the molecules which constitute it. The presence of these reversible hydrogen bonds, which are capable of being broken by a rise in temperature and re-forming at ambient temperature, allows the material according to the invention to have a low viscosity in the molten state, facilitating its use, and optionally a high elongation at break at ambient temperature, without however having a high molecular mass.

The arborescent-branched molecules constituting said material contain a soluble fraction, as well as optionally an insoluble fraction, i.e. a fraction representing from 0.1 to 90% of the weight of the material and which is not soluble in any proportion in any solvent. The number average molecular mass of the soluble fraction is preferably comprised between 300 and 300,000 g/mol, as measured by GC.

According to an embodiment of the invention, the average number of associative end groups per molecule is at least 1.2, preferably of at least 2, or even at least 2.2.

It is moreover understood that this material can contain molecules other than the arborescent-branched molecules described previously, in particular in the case where compound (A) contains trimers of fatty acids mixed with mono- and/or dimers of fatty acids. Advantageously, the material according to the invention contains at least 25% and, better, at least 50% by number said arborescent-branched molecules.

According to the invention it is preferable that this material also contains intermolecular hydrophobic bonds, advantageously due to interactions between alkyl groups borne by each of the arborescent-branched molecules described previously. By "alkyl", is meant within the meaning of the invention side groups ($C_nH_{2n+1}$) and not alkylene chains ($C_nH_{2n}$), for example. In a particularly preferred manner, each of these molecules comprises $C_6$-$C_{24}$ alkyl chains, advantageously in greater numbers than said associative end groups. They can in particular be provided by the compounds (A), in particular when they are trimers of fatty acids.

Compounds (A), (B) and (C) described previously can be introduced, in the method according to the invention, in the molten state or via a solvent.

The proportions of (A), (B) and (C) used in the method according to the invention determine the mechanical characteristics of the material obtained.

This, material advantageously has elastomeric properties, i.e. the property of being able to be subjected to uniaxial deformation at ambient temperature and to recover its initial dimension once this stress is removed, with a permanent deformation of less than 5% of its initial dimension.

It can in particular be used to manufacture seals, thermal or acoustic insulation, tyres, cables, cladding, soles of footwear, packaging, coatings (paints, films, cosmetics), patches (cosmetic or dermo-pharmaceutical) or other systems for trapping and releasing active ingredients, wound dressings, flexible hose clips, vacuum tubes, pipes and hoses for conveying fluids, and generally components requiring good resistance to tearing and/or fatigue, rheological additives or additives for hot-melt glues and adhesives.

In these applications, the material according to the invention can be used as it is or in single-phase or multi-phase mixtures, with one or more compounds such as petroleum cuts, solvents, mineral and organic fillers, plasticizers, tackifying resins, anti-oxidants, pigments and/or colorants, for example, in emulsions, suspensions or solutions.

In a variant, this material can be used for the manufacture of a cosmetic composition usually containing a physiologically acceptable medium, i.e. compatible with keratinous substances.

The invention will be better understood in light of the following example, given for the purposes of illustration only and is not intended to restrict the scope of the invention, defined by the attached claims.

EXAMPLE

Method for Preparing a Material According to the Invention 6.50 g of a diol dimer (Pripol® 2033, hydroxy index=207 (mg of KOH/g), i.e. 24 mmol of alcohol functions) and 14.30 g of acid trimer (Pripol® 1040 (acid index=188 mg of KOH/g, i.e. 48 mmol of acid functions) are introduced into a 100 ml flask equipped with a magnetic stirrer, a feed of nitrogen via a plunger tube, a Soxhlet extractor surmounted by a condenser and a system of heating by an oil bath. 100 µl of sulphuric acid aqueous solution at 36% by mass) and 50 ml of toluene are also introduced. The Soxhlet cartridge was filled with 20 g of anhydrous magnesium sulphate. The oil bath was then heated to reflux of the toluene, the reaction is monitored by observing the reduction in the infrared signal of the acid at 1710 cm-1 and the increase in that of the ester at 1740 cm-1. After reacting for 2 hours at 140° C. (temperature of the oil bath), it is noted that these bands no longer exhibit any particular change. 3.08 g of UDETA (24 mmol) is then added and the mixture is left to react again for 3 hours at 140° C. (temperature of the oil bath)

The solvent is then evaporated off under vacuum at 50° C. using a rotary evaporator then the content of the flask is placed under primary vacuum until degassing is completed (24 hours).

At ambient temperature, the product obtained is a viscoelastic liquid, which is capable, when applied hot (100° C.) to both glass and to a metal surface (aluminium or steel), of spreading easily in order to form an adhesive film.

The invention claimed is:

1. Method for preparing a material formed from arborescent-branched molecules comprising associative groups, the method comprising the following successive steps:
   (a) the reaction of at least one compound (A) that is at least trifunctional bearing first, second and third functions which are identical or different and chosen from acid, ester or acyl chloride functions, with at least one compound (B) that is at least bifunctional having at least two functions which are identical or different and chosen from epoxy, alcohol or amine functions, the functions of compound (B) reacting with the first functions of compound (A), wherein the number ratio of the functions of compound (B) to the sum of the first functions of compound (A) ranges from 0.1 to 0.8, to obtain a compound or compounds from step (a) which still contains free acid, ester or acyl chloride functions; and
   (b) the reaction of the compound or compounds obtained in step (a) with at least one compound (C) bearing, on the one hand, at least one reactive group capable of reacting with the second functions of (A) which reactive group is chosen from the primary or secondary amine or alcohol groups, and, on the other hand, at least one associative group,
   said compound (C) being of formula (C1), (C2) or (C3):

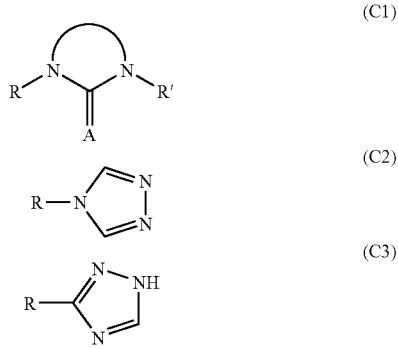

where
R denotes a unit containing at least one primary or secondary amine or alcohol group,
R' denotes a hydrogen atom, and
A denotes an oxygen or sulphur atom or an —NH group.

2. Method according to claim 1, wherein compound (A) has from 5 to 100 carbon atoms.

3. Method according to claim 1, wherein compound (A) is a trimer of a fatty acid of vegetable origin.

4. Method according to claim 3, wherein compound (A) is a trimer of at least one of the following acids: undecylenic acid, myristoleic acid, palmitoleic acid, oleic acid, linoleic acid, linolenic acid, ricinoleic acid, eicosenoic acid, docosenoic acid, eicosapentaenoic acid or docosahexaenoic acid.

5. Method according to claim 1, wherein compound (B) is a diepoxide.

6. Method according to claim 5, wherein compound (B) is chosen from: bisphenol A diglycidyl ethers, bisphenol F diglycidyl ether, tetrabromo bisphenol A diglycidyl ether, or hydroquinone diglycidyl ethers, ethylene glycol diglycidyl ether, propylene glycol diglycidyl ether, butylene glycol diglycidyl ether, neopentyl glycol diglycidyl ether, 1,4-butanediol diglycidyl ether, 1,6-hexanediol diglycidyl ether, cyclohexanedimethanol diglycidyl ether, polyethylene glycol diglycidyl ether, polypropylene glycol diglycidyl ether, polytetramethylene glycol diglycidyl ether, resorcinol diglycidyl ether, neopentylglycol diglycidyl ether, bisphenol A polyethylene glycol diglycidyl ether, bisphenol A polypropyleneglycol diglycidyl ether, or terephthalic acid diglycidyl ester, or mixtures thereof.

7. Method according to claim 1, wherein compound (B) is a diol.

8. Method according to claim 7, wherein compound (B) is chosen from: ethylene glycol, propylene glycol, tetramethylene glycol, hexamethylene glycol, octanediol, nonanediol, decanediol, diethylene glycol, dipropylene glycol, triethylene glycol, tetraethylene glycol, polyethylene glycol, polypropylene glycol, polytetramethylene glycol, polyesters with hydroxy ends, polybutadienes with hydroxy ends, polydimethylsiloxanes with hydroxy ends, polyisobutylenes with hydroxy ends, polybutadiene-co-acrylonitrile copolymers with hydroxy ends, or diol dimers originating from fatty acids or mixtures thereof.

9. Method according to claim 1, wherein compound (C) is chosen from: 2-aminoethylimidazolidone (UDETA), 1-(2-[(2-aminoethyl)amino]ethyl)imidazolidone (UTETA), 1-(2-{2-[(2-aminoethylamino]ethyl}amino)ethyl]imidazolidone (UTEPA), 3-amino-1,2,4-triazole (3-ATA) or 4-amino-1,2,4-triazole (4-ATA).

10. Method according to claim 1, wherein the number ratio of the functions of compound (B) to the sum of the first functions of compound (A) ranges from 0.3 to 0.8.

11. Method according to claim 1, wherein compound (C) is of the formula (C1) wherein A is an oxygen atom.

12. Method according to claim 1, wherein compound (A) has from 12 to 100 carbon atoms.

13. Method according to claim 1, wherein compound (A) has from 24 to 90 carbon atoms.

14. Method according to claim 1, wherein compound (A) is a trimer of a fatty acid of vegetable origin and compound (B) is a diepoxide or diol.

* * * * *